(12) United States Patent
Woo et al.

(10) Patent No.: US 6,969,483 B1
(45) Date of Patent: *Nov. 29, 2005

(54) AUTOCLAVABLE, NON-ADHERENT, HEAT SEALABLE POLYMER BLENDS FOR FABRICATING MONOLAYER AND MULTIPLE LAYERED FILMS

(75) Inventors: Lecon Woo, Libertyville, IL (US); Sherwin Shang, Vernon Hills, IL (US); Michael T. K. Ling, Vernon Hills, IL (US); Yuan-pang Samuel Ding, Vernon Hills, IL (US); Tahua Yang, Darien, IL (US); Craig Sanford, Wheeling, IL (US); Tao Chang, Ames, IA (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/526,357

(22) Filed: Mar. 16, 2000

(51) Int. Cl.⁷ ............................ C08L 23/00; C08L 23/16
(52) U.S. Cl. ..................... 264/405; 428/500; 525/191; 525/201; 525/240
(58) Field of Search ................................ 525/240, 201, 525/191; 264/405; 428/500

(56) References Cited

U.S. PATENT DOCUMENTS

| | | |
|---|---|---|
| 2,705,223 A | 3/1955 | Renfrew et al. |
| 3,255,923 A | 6/1966 | Soto |
| 3,375,300 A | 3/1968 | Ropp |
| 3,772,136 A | 11/1973 | Workman |
| 3,912,843 A | 10/1975 | Brazier |
| 3,937,758 A | 2/1976 | Castagna |

(Continued)

FOREIGN PATENT DOCUMENTS

CA  1125229  6/1982

(Continued)

OTHER PUBLICATIONS

PCT International Search Report.

*Primary Examiner*—Jeffrey Mullis
(74) *Attorney, Agent, or Firm*—Ira D. Finkelstein; Paula J. F. Kelly; Robert M. Barrett

(57) ABSTRACT

The present invention provides a polymer blend for fabricating monolayer films or a layer within a multilayer film. The blend has a first component and a second component. The first component is selected from the group of: (1) an ethylene and α-olefin copolymer having a density of less than about 0.915 g/cc, (2) lower alkyl acrylates, (3) lower alkyl substituted alkyl acrylates and (4) ionomers. The first component should be present in an amount from about 99% to about 55% by weight of the blend. The second component in an amount by weight of the blend from 45% to about 1% and consists of one or more polymers of the group: (1) propylene containing polymers, (2) polybutene polymers, (3) polymethylpentene polymers, (4) cyclic olefin containing polymers and (5) bridged polycyclic hydrocarbon containing polymers. When the blend is fabricated into a film it has a modulus of elasticity when measured in accordance with ASTM D882 of less than about 60,000 psi, an internal haze when measured in accordance with ASTM D1003 of less than about 25%, an internal adhesion ranking of greater than about two, a sample creep at 120° C. under 27 psi loading of less than or equal to 150% for a film having a thickness from about 5 mils to about 15 mils, and the film being capable or being heat sealed into a container having seals wherein the seals remain intact when the container is autoclaved at 121° C. for one hour.

79 Claims, 3 Drawing Sheets

U.S. PATENT DOCUMENTS

| | | |
|---|---|---|
| 3,995,084 A | 11/1976 | Berger et al. |
| 4,041,103 A | 8/1977 | Davison et al. |
| 4,058,647 A | 11/1977 | Inoue et al. |
| 4,087,587 A | 5/1978 | Shida et al. |
| 4,087,588 A | 5/1978 | Shida et al. |
| 4,095,012 A | 6/1978 | Schirmer |
| 4,147,827 A | 4/1979 | Breidt, Jr. et al. |
| 4,230,830 A | 10/1980 | Tanny et al. |
| 4,233,367 A | 11/1980 | Ticknor et al. |
| 4,311,807 A | 1/1982 | McCullough et al. |
| 4,322,465 A | 3/1982 | Webster |
| 4,322,480 A | 3/1982 | Tuller et al. |
| 4,327,726 A | 5/1982 | Kwong |
| 4,332,655 A | 6/1982 | Berejka |
| 4,387,184 A | 6/1983 | Coquard et al. |
| 4,401,536 A | 8/1983 | Lundell et al. |
| 4,405,667 A | 9/1983 | Christensen et al. |
| 4,407,877 A | 10/1983 | Rasmussen |
| 4,407,888 A | 10/1983 | Crofts |
| 4,417,753 A | 11/1983 | Bacebowski et al. |
| 4,429,076 A | 1/1984 | Saito et al. |
| 4,453,940 A | 6/1984 | Aoyagi et al. |
| 4,465,487 A | 8/1984 | Nakamura et al. |
| 4,479,989 A | 10/1984 | Mahal |
| 4,521,437 A | 6/1985 | Storms |
| 4,548,348 A | 10/1985 | Clements |
| 4,562,118 A | 12/1985 | Maruhashi et al. |
| 4,568,723 A | 2/1986 | Lu |
| 4,588,648 A | 5/1986 | Krueger et al. |
| 4,599,276 A | 7/1986 | Martini |
| 4,627,844 A | 12/1986 | Schmitt |
| 4,636,412 A | 1/1987 | Field |
| 4,640,870 A | 2/1987 | Akazawa et al. |
| 4,643,926 A | 2/1987 | Mueller |
| 4,686,125 A | 8/1987 | Johnston et al. |
| 4,692,361 A | 9/1987 | Johnson et al. |
| 4,707,389 A | 11/1987 | Ward |
| 4,724,028 A | 2/1988 | Zabielski et al. |
| 4,724,176 A | 2/1988 | Sun |
| 4,726,997 A | 2/1988 | Mueller et al. |
| 4,732,795 A | 3/1988 | Ohya et al. |
| 4,734,327 A | 3/1988 | Vicik |
| 4,735,855 A | 4/1988 | Wofford et al. |
| 4,740,582 A | 4/1988 | Coquard et al. |
| 4,753,222 A | 6/1988 | Morishita |
| 4,760,114 A | 7/1988 | Haaf et al. |
| 4,764,404 A | 8/1988 | Genske et al. |
| 4,767,651 A | 8/1988 | Starczewski et al. |
| 4,772,497 A | 9/1988 | Maasola |
| 4,778,697 A | 10/1988 | Genske et al. |
| 4,792,488 A | 12/1988 | Schirmer |
| 4,795,782 A | 1/1989 | Lutz et al. |
| 4,800,129 A | 1/1989 | Deak |
| 4,803,102 A | 2/1989 | Raniere et al. |
| 4,834,755 A | 5/1989 | Silvestrini et al. |
| 4,855,356 A | 8/1989 | Holub et al. |
| 4,856,259 A | 8/1989 | Woo et al. |
| 4,856,260 A | 8/1989 | Woo et al. |
| 4,863,996 A | 9/1989 | Nakazima et al. |
| 4,871,799 A | 10/1989 | Kobayashi et al. |
| 4,873,287 A | 10/1989 | Holub et al. |
| 4,877,682 A | 10/1989 | Sauers et al. |
| 4,885,119 A | 12/1989 | Mueller et al. |
| 4,892,604 A | 1/1990 | Measells et al. |
| 4,910,085 A | 3/1990 | Raniere et al. |
| 4,923,470 A | 5/1990 | Dumican |
| 4,929,479 A | 5/1990 | Shishido et al. |
| 4,957,966 A | 9/1990 | Nishio et al. |
| 4,957,967 A | 9/1990 | Mizuno et al. |
| 4,966,795 A | 10/1990 | Genske et al. |
| 4,977,213 A | 12/1990 | Giroud-Abel et al. |
| 4,996,054 A | 2/1991 | Pietsch et al. |
| 5,006,601 A | 4/1991 | Lutz et al. |
| 5,017,652 A | 5/1991 | Abe et al. |
| 5,034,457 A | 7/1991 | Serini et al. |
| 5,034,458 A | 7/1991 | Serini et al. |
| 5,053,457 A | 10/1991 | Lee |
| 5,055,328 A | 10/1991 | Evert et al. |
| 5,066,290 A | 11/1991 | Measells et al. |
| 5,071,686 A | 12/1991 | Genske et al. |
| 5,071,911 A | 12/1991 | Furuta et al. |
| 5,071,912 A | 12/1991 | Furuta et al. |
| 5,075,376 A | 12/1991 | Furuta et al. |
| 5,079,295 A | 1/1992 | Furuta et al. |
| 5,085,649 A | 2/1992 | Flynn |
| 5,093,164 A | 3/1992 | Bauer et al. |
| 5,093,194 A | 3/1992 | Touhsaent et al. |
| 5,094,921 A | 3/1992 | Itamura et al. |
| 5,108,844 A | 4/1992 | Blemberg et al. |
| 5,110,642 A | 5/1992 | Genske |
| 5,116,906 A | 5/1992 | Mizuno et al. |
| 5,129,894 A | 7/1992 | Sommermeyer et al. |
| 5,132,363 A | 7/1992 | Furuta et al. |
| 5,145,731 A | 9/1992 | Lund et al. |
| 5,154,979 A | 10/1992 | Kerschbaumer et al. |
| 5,159,004 A | 10/1992 | Furuta et al. |
| 5,164,267 A | 11/1992 | D'Heur et al. |
| 5,176,634 A | 1/1993 | Smith et al. |
| 5,176,956 A | 1/1993 | Jevne et al. |
| 5,183,706 A | 2/1993 | Bekele |
| 5,185,189 A | 2/1993 | Stenger et al. |
| 5,189,091 A | 2/1993 | Laughner |
| 5,194,316 A | 3/1993 | Horner et al. |
| 5,196,254 A | 3/1993 | Akiyama |
| 5,206,290 A | 4/1993 | Mizuno et al. |
| 5,212,238 A | 5/1993 | Schelbelhoffer et al. |
| 5,218,048 A | 6/1993 | Abe et al. |
| 5,218,049 A | 6/1993 | Yamamoto et al. |
| 5,230,934 A | 7/1993 | Sakano et al. |
| 5,230,935 A | 7/1993 | Delimoy et al. |
| 5,238,997 A | 8/1993 | Bauer et al. |
| 5,244,971 A | 9/1993 | Dekoninck |
| 5,258,230 A | 11/1993 | LaFleur et al. |
| 5,272,210 A | 12/1993 | Galante |
| 5,272,236 A | 12/1993 | Lai et al. |
| 5,278,231 A | 1/1994 | Chundury |
| 5,288,799 A | 2/1994 | Schmid et al. |
| 5,290,856 A | 3/1994 | Okamoto et al. |
| 5,306,542 A | 4/1994 | Bayer |
| 5,312,867 A | 5/1994 | Mitsuno et al. |
| 5,317,059 A | 5/1994 | Chundury et al. |
| 5,342,886 A | 8/1994 | Glotin et al. |
| 5,348,794 A | 9/1994 | Takahashi et al. |
| 5,356,676 A | 10/1994 | Widdern et al. |
| 5,371,141 A | 12/1994 | Gelles et al. |
| 5,378,543 A | 1/1995 | Murata et al. |
| 5,378,800 A | 1/1995 | Mok et al. |
| 5,387,645 A | 2/1995 | Montag et al. |
| 5,445,893 A | 8/1995 | Mueller et al. |
| 5,783,638 A | 7/1998 | Lai et al. |
| 5,792,824 A | 8/1998 | Natori |
| 5,795,945 A | 8/1998 | Natori |
| 5,854,349 A | 12/1998 | Abe et al. |
| 5,863,986 A | 1/1999 | Herrmann-Schönherr et al. |
| 5,879,768 A | 3/1999 | Falla et al. |
| 6,410,651 B1 * | 6/2002 | Castellani et al. .......... 525/232 |
| 6,503,637 B1 * | 1/2003 | Van Loon .................. 428/516 |
| 6,613,187 B1 * | 9/2003 | Ding et al. ................. 156/334 |
| 6,743,523 B1 * | 6/2004 | Woo et al. .................. 428/516 |

FOREIGN PATENT DOCUMENTS

| | | |
|---|---|---|
| DE | 41 42 271 A1 | 6/1993 |

| | | |
|---|---|---|
| EP | 92897 | 2/1983 |
| EP | 0 283 164 | 9/1988 |
| EP | 0 291 208 | 11/1988 |
| EP | 0 468 768 A1 | 1/1992 |
| EP | 0 497 567 | 8/1992 |
| EP | 446505 A1 | 6/1993 |
| EP | 0 634 270 A1 | 1/1995 |
| EP | 0 636 473 A1 | 2/1995 |
| FR | 2688511 | 9/1993 |
| GB | 2 177 974 A | 2/1987 |
| JP | 09/131837 | 5/1997 |
| WO | WO83/00158 | 1/1983 |
| WO | WO 86/07010 | 12/1986 |
| WO | WO 93 23093 | 11/1993 |
| WO | WO 95/13918 | 5/1995 |
| WO | WO 97/22655 | 6/1997 |
| WO | WO 97/36741 * | 10/1997 |
| WO | WO 01/18112 A2 | 5/2002 |

* cited by examiner

FIG. 1
FIG. 2
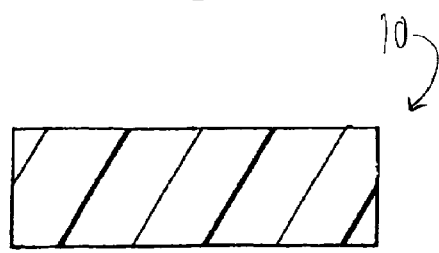
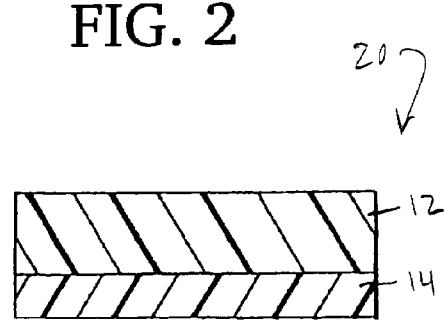
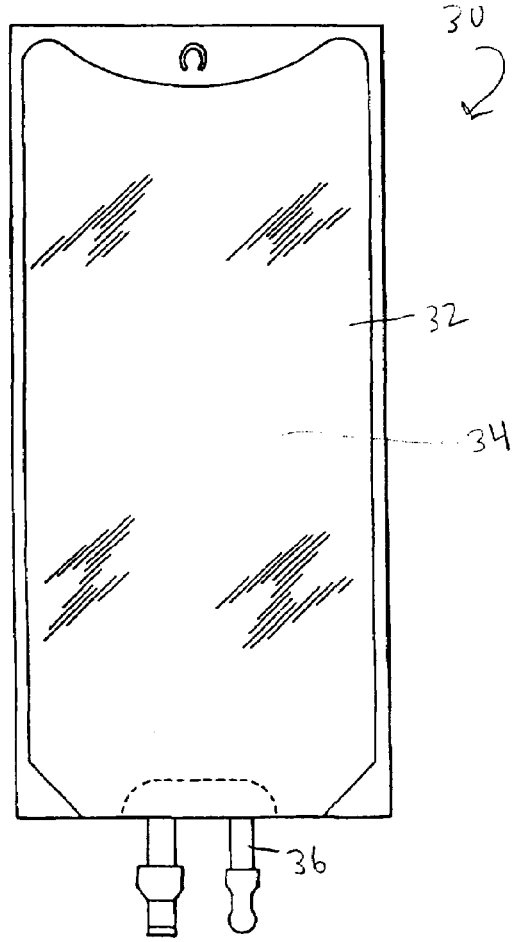
FIG. 3

AUTOCLAVABLE, NON-ADHERENT, HEAT SEALABLE POLYMER BLENDS FOR FABRICATING MONOLAYER AND MULTIPLE LAYERED FILMS

TECHNICAL FIELD

The present invention relates generally to polymer blends for fabricating films and more particularly films that have low distortion and are non-adherent upon steam sterilization, are heat sealable and are suitable for fabricating into flexible medical containers.

BACKGROUND OF THE INVENTION

In the medical field, where beneficial agents are collected, processed and stored in containers, transported, and ultimately delivered through tubes by infusion to patients to achieve therapeutic effects, materials which are used to fabricate the containers must have a unique combination of properties. For example, visual inspection of solutions for particulate contamination requires an optically transparent container. The material which forms the wall must be sufficiently flexible to infuse a solution by collapsing the container walls, without introducing air into the container. The material must maintain its flexibility and toughness over a wide range of temperatures. The material must maintain its flexibility and toughness at low temperatures because some solutions, for example, certain premixed drug solutions, are stored and transported in containers at temperatures such as −25 to −30° C. to minimize the drug degradation. The material must also be functional and resist distortion at high temperatures to withstand the heat of steam sterilization; a process which most medical fluid containers and nutritional products are subjected to prior to shipment. The sterilization process usually includes exposing the container to steam at temperatures typically 121° C. and at elevated pressures.

For ease of manufacture into useful articles, it is desirable that the material be sealable using heat sealing techniques. The material therefore must maintain sufficient thermoplastic properties to melt upon heating.

A further requirement is to minimize the environmental impact upon the disposal of the article fabricated from the material after its intended use. For those articles that are disposed of in landfills, it is desirable to minimize or avoid the incorporation of low molecular weight leachable components to construct the article. Further benefits are realized by using a material that allows thermal reprocessing of scrap material produced during manufacturing.

For those containers which are disposed of through incineration to minimize biological hazards, it is desirable to use a material that minimizes or eliminates the formation of environmentally undesirable and corrosive inorganic acids.

It is also desirable that the material be free from or have a low content of low molecular weight additives such as plasticizers, stabilizers and the like which could be released into the medications or biological fluids.

Due to its ability to meet a wide variety of functional requirements, flexible polyvinyl chloride (PVC) has frequently been the material of choice for medical bag applications. PVC also offers the distinct advantage of being one of the most cost-effective materials for constructing devices that meet the above requirements. However, PVC has a number of disadvantages in the marketplace. These disadvantages include incompatibility of PVC compounds with certain drugs, concerns regarding chlorine content and its effects on the environment and a growing negative market perception of PVC in general. Thus, many materials have been devised to replace PVC. However, most alternate materials are too expensive to implement and still do not meet all of the above requirements.

Polyolefins and polyolefin alloys have been developed which meet many of the requirements of medical containers and tubing, without the disadvantages associated with PVC. Polyolefins typically are compatible with medical applications because they have relatively low extractability to fluids. Most polyolefins are environmentally sound as they do not generate harmful degradants upon incineration, and are suitable for thermoplastic recycling. Many polyolefins are cost effective materials that may provide an economic alternative to PVC. However, there are many hurdles to overcome to replace all the favorable attributes of PVC with a polyolefin.

For example, problems have been encountered in using certain polyolefins to fabricate medical tubing. Such tubing has been found to have poor surface characteristics so that it is readily susceptible to cutting, shredding or scoring when clamping the tubing using a slide clamp. Also, certain polyolefins that have favorable modulus attributes, such as ultra-low density polyethylenes, have melting point temperatures below that reached during an autoclave process.

It is well known that cross linking by chemical agents or by high energy ionizing radiation increases heat resistance of the polymer matrix. The chemical crosslinks are covalent bonds across separate polymer chains that greatly retard the tendency to deform and flow at high temperatures—even above the melting point of the polymer. For example, U.S. Pat. No. 4,465,487 assigned to Terumo discloses fabricating steam autoclavable medical containers by irradiating ethylene vinyl acetate copolymers with high energy (2 Mev) electron beams at doses between 50 kGy and 100 kGy to achieve gel contents of between 50% and 85%. The '487 Patent discloses that if the EVA sidewalls of the container are irradiated to achieve a gel content of about 50% or higher before being sealed together they are easily peeled apart. (Col. 4, lines 20–30). Accordingly, the '487 patent discloses irradiating the sidewalls of the container after sealing the container into a pouch leaving only a port area unsealed.

Similarly, U.S. Pat. No. 4,453,940 discloses fabricating medical containers from EVA and other materials. The '940 patent also discloses the step of increasing the autoclave resistance of EVA by cross-linking the material with high energy electron beam. The '940 patent warns that if the cross-linking exceeds 50% the use of heat sealing becomes impossible. (Col. 4, lines 27–35).

U.S. Pat. No. 4,401,536 discloses crosslinking semi-rigid containers composed of blends of polypropylene and EVA or EEA. This patent does not disclose the use of ethylene alpha olefins with polypropylene. It also discloses that irradiation before forming results in articles with poor heat sealability (Col. 4, lines 25–28).

U.S. Pat. Nos. 4,892,604 and 5,066,290 both assigned to the present assignee, disclose a medical container with a coextruded high density polyethylene skin layer and a core layer of an ethylene vinyl acetate copolymer having about 18% vinyl acetate content. After the container is fabricated by conventional radio frequency heat seal, the assembly is subjected to ionizing radiation of about 100 kGy from a high energy electron beam accelerator of about 5 Mev. The high density polyethylene layer acts as a moisture and gas transmission barrier to maintain the sterile fluid content at a relatively constant concentration as required by various pharmacopoeia of the world. However, several serious deficiencies were apparent in this material construction: 1) to fabricate a container from this material construction the container must be fabricated before the cross-linking process, since the cross-linked EVA layer is difficult if not impossible to seal (this renders the manufacturing process very inefficient); and 2) the radiation dose required for sufficient cross-linking also releases significant quantities of acetic acid—a by-product of the radiation exposure. Since the HDPE presents a barrier to gas transmission, the trapped acetic acid can render the fluid contents quite acidic—a very undesirable outcome.

U.S. Pat. No. 4,643,926 assigned to W. R. Grace discloses fabricating a medical solution container from a multilayered material where, in certain embodiments, the layer intended to be heat sealed is constructed with polypropylene as the main ingredient. Since it is well known that polypropylenes undergo chain scission when exposed to radiation, the heat seal layer remained thermoplastic and capable of being heat-sealed to similar surfaces. Therefore, the entire multilayer film can be heat-sealed and survive autoclaving. However, the complexity of the multilayer construction and the possible need of washing and incorporating acid scavenging compounds in the film (See U.S. Pat. No. 5,445,893) to remove the acidic by-products of irradiating EVA renders the process quite complicated and the cost very high. Further, since the film is constructed of several very dissimilar materials, process recycling of the edge trim and other film scraps is very difficult and impractical without greatly reducing the optical and mechanical properties.

U.S. Pat. No. 5,055,328 discloses a multilayer differentially cross-linked film where the heat-sealed layer contains additional antioxidants to retard cross-linking and to facilitate heat-sealing post cross-linking. Likewise, Canadian Patent 1,125,229 discloses another differential cross-linked multilayer film where the outer layer contains a cross-link enhancer. However, these constructions are all multilayer constructions and do not address the issue of self adhesion during autoclaving.

U.S. Pat. No. 4,724,176 to Sun discloses a multilayer, oriented, heat shrinkable container with a radiation cross-linked outer layer and, by controlling the irradiation process, a non cross-linked inner seal layer. The inner and outer layers can be of EVA copolymers. This container is designed to shrink upon application of heat, and, therefore, would be unsuitable for a container that must maintain substantially its entire volume after an autoclave process.

The main objective of the present invention is to provide polymeric materials that are, overall, superior to those materials, of which we are aware, which have been heretofore known in the art or have been commercially used or marketed. The properties of such materials include flexibility, optical transparency for visual inspection, and sufficient thermal resistance to withstand a steam sterilization process at temperatures up to 121° C. without experiencing significant distortion or self adhesion. The materials should also be non-oriented, non-adherent and capable of being sealed using heat sealing techniques. The materials should also be substantially free of low molecular weight leachable additives, and capable of safe disposal by incineration without the generation of significant amounts of corrosive inorganic acids. Finally, the material should serve as a cost-effective alternative to various PVC formulations currently being used for medical devices.

U.S. Pat. No. 5,879,768 discloses a pouch for packaging flowable materials fabricated from a material having a seal layer of a polymeric composition comprising: (A) 10 to 100 percent of a mixture of (1) from 5 to 95% of at least one homogeneously branched substantially linear ethylene/α-olefin interpolymer, and (2) from 5 to 95% of high pressure low density polyethylene having a density from 0.916–0.930 g/cc; and (B) from 0–90% of one polymer selected from the group consisting of an ultra low density polyethylene, a linear low density polyethylene, a high pressure low density polyethylene, an ethylene vinyl acetate copolymer, and a homogeneously branched linear ethylene polymer. The '768 patent does not disclose exposing this blend to radiation nor does it disclose blending the homogeneously branched, substantially linear ethylene/α-olefin interpolymer with polypropylene.

When more than one polymer is blended to form an alloying composition, it is difficult to achieve all of the above objectives simultaneously. For example, many alloys produce significant light scattering; thus, they fail to meet the optical clarity objective. The light scattering intensity (measured by haze) depends on the domain size of components in the micrometer ($\mu$) range, and the proximity of the refractive indices of the components. As a general rule, the selection of components that can be satisfactorily processed into very small domain sizes, and yet with a minimum of refractive index mismatches, is a difficult task. The present invention is provided to solve these and other problems.

SUMMARY OF THE INVENTION

The present invention provides polymer blends for fabricating monolayer films or a layer within a multilayer film. The blend has a first and a second component. The first component is selected from the group of: (1) ethylene and α-olefin interpolymers having a density of less than about 0.915 g/cc, (2) ethylene and lower alkyl acrylate interpolymers, (3) ethylene and lower alkyl substituted alkyl acrylate interpolymers and (4) ionic polymers, commonly referred to as ionomers. The second component is selected from one or more of the following: (1) propylene containing polymers, (2) butene containing polymers, (3) polymethylpentene containing polymers, (4) cyclic olefin containing polymers and (5) bridged polycyclic hydrocarbon containing polymers. The first component is present in an amount from about 99% to about 55% and the second component is present in an amount by weight of about the blend from about 45% to about 1%.

The blend when fabricated into a film has a modulus of elasticity when measured in accordance with ASTM D882 of less than about 60,000 psi, an internal haze when measured in accordance with ASTM D1003 of less than about 25%, self adhesion ranking greater than about 2 as defined below, slight or no adhesion to overpouch materials, has a sample creep at 120° C. at about 27 psi loading of less than or equal to 150%, and the film can be heat sealed into a container having seals wherein the seals remain intact when a liquid filled container is autoclaved at 121° C. for one hour.

The present invention also provides a non-PVC, non-oriented, monolayer film having sufficient heat distortion resistance to withstand steam sterilization conditions. The film is fabricated from blend of a first and a second component. The first component is selected from the group of: (1) ethylene and α-olefin interpolymers having a density of less than about 0.915 g/cc, (2) ethylene and lower alkyl acrylate interpolymers, (3) ethylene and lower alkyl substituted alkyl acrylate interpolymers and (4) ionic polymers, commonly referred to as ionomers. The second component is selected from one or more of the following: (1) propylene containing polymers, (2) butene containing polymers, (3) polymethylpentene containing polymers, (4) cyclic olefin containing polymers and (5) bridged polycyclic hydrocarbon containing polymers. The first component is present in an amount from about 99% to about 55% and the second component is present in an amount by weight of the blend from about 45% to about 1%.

The film has a modulus of elasticity when measured in accordance with ASTM D882 of less than about 60,000 psi, an internal haze when measured in accordance with ASTM D1003 of less than about 25%, self adhesion ranking greater than about 2 as defined below, slight or no adhesion to overpouch materials, has a sample creep at 120° C. at about 27 psi loading of less than or equal to 150%, and the film can be heat sealed into a container having seals wherein the seals remain intact when a liquid filled container is autoclaved at 121° C. for one hour.

The present invention further provides a method for fabricating a non-PVC and non oriented film. The method includes the steps of: providing a first and a second component, mixing the first component with the second component to define a blend, extruding the blend into a film and exposing the film to electron beam radiation. The first component is selected from the group of: (1) ethylene and α-olefin interpolymers having a density of less than about 0.915 g/cc, (2) ethylene and lower alkyl acrylate interpolymers, (3) ethylene and lower alkyl substituted alkyl acrylate interpolymers and (4) ionic polymers, commonly referred to as ionomers. The second component is selected from one or more of the following: (1) propylene containing polymers, (2) butene containing polymers, (3) polymethylpentene containing polymers, (4) cyclic olefin containing polymers and (5) bridged polycyclic hydrocarbon containing polymers. The first component is present in an amount from about 99% to about 55% and the second component is present in an amount by weight of the blend from about 45% to about 1%.

The film has a modulus of elasticity when measured in accordance with ASTM D882 of less than about 60,000 psi, an internal haze when measured in accordance with ASTM D1003 of less than about 25%, self adhesion ranking greater than about 2 as defined below, slight or no adhesion to overpouch materials, has a sample creep at 120° C. at about 27 psi loading of less than or equal to 150%, and the film can be heat sealed into a container having seals wherein the seals remain intact when a liquid filled container is autoclaved at 121° C. for one hour.

BRIEF DESCRIPTION OF THE DRAWINGS

FIG. 1 is a cross-sectional view of a monolayer film of the present invention;

FIG. 2 is a cross-sectional view of a multiple layered film of the present invention;

FIG. 3 is a material container fabricated from a film of the present invention;

DETAILED DESCRIPTION

Figures 4, 5:
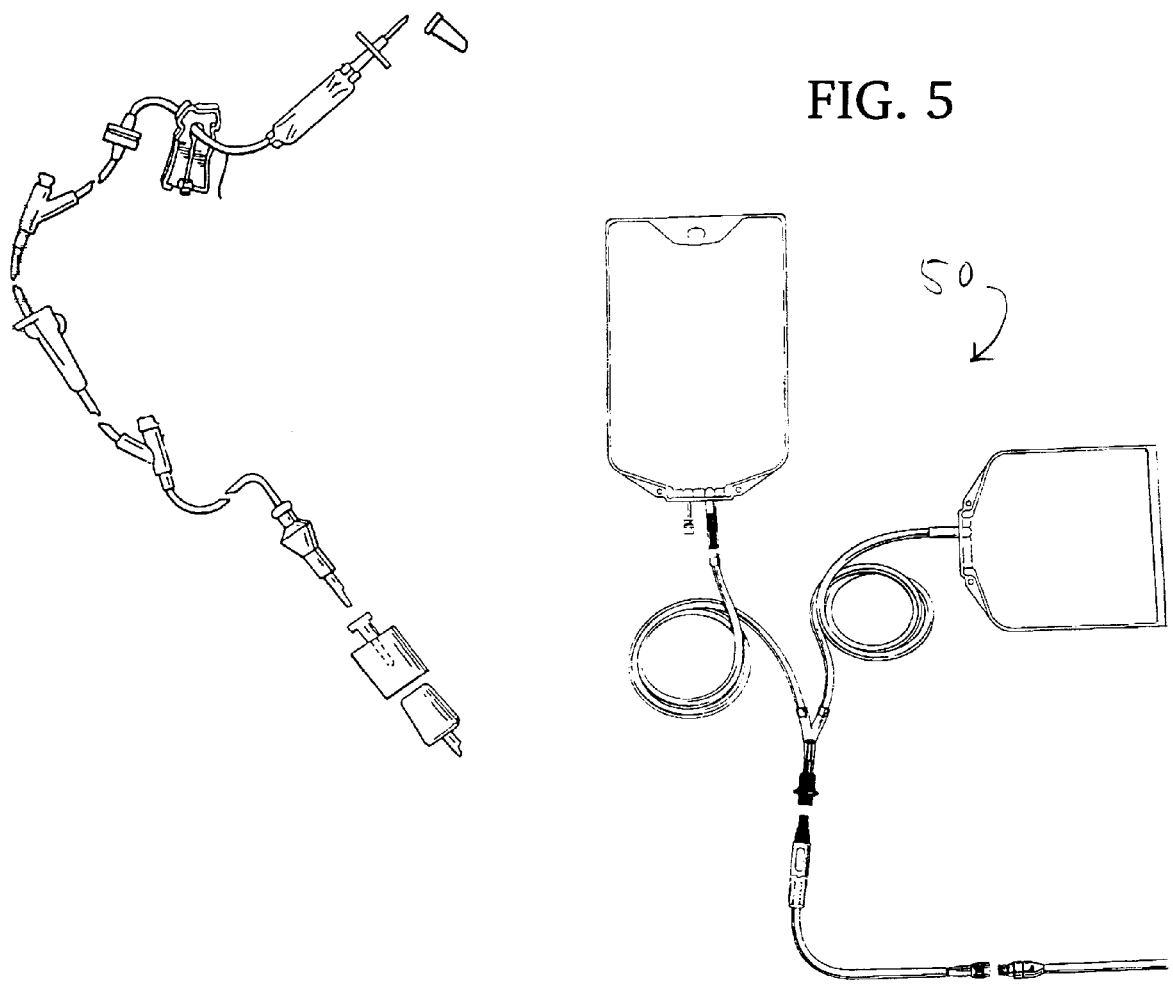
FIG. 4 is an I.V. fluid administration set.
FIG. 5 is a peritoneal dialysis container and tubing set.

The present invention is susceptible of embodiments in many different forms. Preferred embodiments of the invention are disclosed with the understanding that the present disclosure is to be considered as an exemplification of the principles of the invention and is not intended to limit the broad aspects of the invention to the embodiments illustrated.

I. Polymer Blends and Monolayer Films Therefrom

FIG. 1 shows a monolayer film 10 of the present invention. The monolayer film 10 is fabricated from a polymer blend having a first component and a second component. The first component is selected from the group of: (1) ethylene and α-olefin interpolymers having a density of less than about 0.915 g/cc; (2) ethylene and lower alkyl acrylate interpolymers, (3) ethylene and lower alkyl substituted alkyl acrylate interpolymers and (4) ionic polymers, commonly referred to as ionomers. The first component is present in an amount from about 99% to about 55% by weight of the blend, more preferably from about 60%–85% and most preferably from about 65%–80%.

The second component is selected from the group consisting of: (1) propylene containing polymers, (2) butene containing polymers, (3) polymethyl pentene containing polymers, (4) cyclic olefin containing polymers and (5) bridged polycyclic hydrocarbon containing polymers. The second component is present in an amount by weight of the blend from about 45% to about 1%, more preferably from about 15%–40% and most preferably from about 20%–35%.

The film has a modulus of elasticity when measured in accordance with ASTM D882 of less than about 60,000 psi, an internal haze when measured in accordance with ASTM D1003 of less than about 25%, self adhesion ranking greater than about two (as defined below), slight or no adhesion to overpouch materials, has a sample creep at 120° C. at about 27 psi loading of less than or equal to 150%, and the film can be heat sealed into a container having seals wherein the seals remain intact when a liquid filled container is autoclaved at 121° C. for one hour.

As used herein, the term "interpolymer" includes copolymers, terpolymers either random or block.

Suitable ethylene and α-olefin interpolymers preferably have a density, as measured by ASTM D-792 of less than about 0.915 g/cc and are commonly referred to as very low density polyethylene (VLDPE), ultra low density ethylene (ULDPE) and the like. The α-olefin should have from 3–17 carbons, more preferably from 4–12 and most preferably 4–8 carbons. In a preferred form of the invention, the ethylene and α-olefin copolymers are obtained using single site catalysts. Suitable single site catalyst systems, among others, are those disclosed in U.S. Pat. Nos. 5,783,638 and 5,272,236. Suitable ethylene and α-olefin copolymers include those sold by Dow Chemical Company under the AFFINITY tradename, Dupont-Dow under the ENGAGE tradename and Exxon under the EXACT and PLASTOMER tradenames.

The term "lower alkyl acrylates" refers to comonomers having the formula set forth in Diagram 1:

Diagram 1

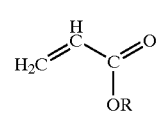

The R group refers to alkanes having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

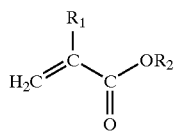

Diagram 2

$R_1$ and $R_2$ are alkanes having 1–17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable propylene containing polymers include those selected from the group consisting of homopolymers of polypropylene, copolymers and terpolymers of propylene with one or more comonomers selected from α-olefins having from 2–17 carbons. Suitable polypropylene copolymers and terpolymers include random or block propylene and ethylene copolymers or random or block propylene/ethylene/butene terpolymers. Suitable propylene and α-olefin copolymers are sold by Montell under the tradename PRO FAX, PRO FAX ULTRA and CATALLOY.

The present invention also contemplates using blends of propylene containing polymers as the second component of the blend. In a preferred form of the invention the blends include at least a first propylene containing polymer and a second propylene containing polymer. The first propylene containing polymer and the second propylene containing polymer can be selected from the propylene homopolymer, copolymers and terpolymers set forth above. In a preferred form of the invention the first propylene containing polymer differs from the second propylene containing polymer in at least one of two ways. The first difference is the first propylene containing polymer preferably should have a melt flow rate of from about 3 times greater and more preferably from about 5 times greater than the melt flow rate of the second propylene containing polymer. The second difference is the first propylene containing polymer preferably has a melting point from at least about 5° C. higher and more preferably from at least about 10° C. higher than that of the second propylene containing polymer. The melting point is measured in accordance with ASTM D3417 (Enthalpies of Fusion and Crystallization of Polymers by Differential Scanning Calorimetry). The first propylene containing polymer can differ from the second propylene containing polymer by the first difference, by the second difference or by both.

Suitable homopolymer and copolymers of cyclic olefins and bridged polycyclic hydrocarbons and blends thereof can be found in U.S. Pat. Nos. 5,218,049, 5,854,349, 5,863,986, 5,795,945, 5,792,824; and European Patent numbers EP 0 291,208, EP 0 283,164, EP 0 497,567 which are incorporated in their entirety herein by reference and made a part hereof.

In a preferred form of the invention, suitable cyclic olefin monomers are monocyclic compounds having from 5 to about 10 carbons in the ring. The cyclic olefins can be selected from the group consisting of substituted and unsubstituted cyclopentene, cyclopentadiene, cyclohexene, cyclohexadiene, cycloheptene, cycloheptadiene, cyclooctene, cyclooctadiene. Suitable substituents include lower alkyl, acrylate derivatives and the like.

In a preferred form of the invention, suitable bridged polycyclic hydrocarbon monomers have two or more rings and more preferably contain at least 7 carbons. The rings can be substituted or unsubstituted. Suitable substitutes include lower alkyl, aryl, aralkyl, vinyl, allyloxy, (meth)acryloxy and the like. The bridged polycyclic hydrocarbons are selected from the group consisting of those disclosed in the above incorporated patents and patent applications. Suitable bridged polycyclic hydrocarbon containing polymers are sold by Ticona under the tradename TOPAS, by Nippon Zeon under the tradename ZEONEX and ZEONOR, by Daikyo Gomu Seiko under the tradename CZ resin, and by Mitsui Petrochemical Company under the tradename APEL.

In a preferred form of the present invention the film will have the following physical characteristics: (1) a modulus of elasticity when measured in accordance with ASTM D882 of less than about 60,000 psi, (2) an internal haze when measured in accordance with ASTM D1003 of less than about 25%, (3) self adhesion ranking greater than about two as defined below, (4) no adhesion to overpouch materials, (5) has a sample creep at 120° C. at about 27 psi loading of less than or equal to 150%, and (6) the film can be heat sealed into a container having seals wherein the seals remain intact when a liquid-filled container is autoclaved at 121° C. for one hour.

The film is also sufficiently flexible to construct flowable material containers. The film has a modulus of elasticity of less than about 60,000 psi, more preferably less than about 40,000 psi, even more preferably less than about 30,000 and most preferably less than about 20,000 psi when measured in accordance with ASTM D-882. When the flowable material container is an I.V. container it is desirable the container collapse or substantially collapse upon draining, and, therefore, should have a modulus of elasticity of less than about 40,000 psi, more preferably less than about 30,000 psi, and even more preferably less than about 20,000 when measured in accordance with ASTM D-882.

For the purposes of this invention, self adhesion is defined as the tendency of the film to adhere to itself during autoclaving. This property can be determined with the following test. Film strips are cut 8"×2", with the larger dimension in the machine direction. These strips are rolled into 2" long tubes approximately 0.5" in diameter. The wound film is held in place by compressing the film layers together at one end with a paper clip. The tubes are then placed in a steam autoclave at 121° C. for 30 minutes. The samples are allowed to cool for at least one hour. The film is then unwound. The resistance to unwinding and relative damage to the film is ranked as shown in Table 1 as follows:

Table 1

Rank Observed Result
1 The film cannot be unwound without destroying the film.
2 The film is difficult to peel and significant surface damage results.
3 Some resistance to peeling and minor surface damage are noted.
4 Slight resistance to peeling noted with little or no surface damage.
5 No peel resistance and no surface damage noted.

Ranks are determined by three or more individuals and recorded as an average.

Adhesion to over pouch materials is determined by the following qualitative test. One inch wide strips of film are sealed into typical over pouch bags (medium or high density polyethylene). The over pouch bag is then placed into a laboratory autoclave at 252° F. and 24.5 psig gauge pressure for one hour. After autoclaving, the bags are cut open and the strips removed. If the films separate from the over pouch without leaving damage marks on the film surface, a ranking of no adhesion (N) is given If the film separation produces visible damage, a ranking is given (Y) indicating that tack to the over pouch is present. A ranking to indicate slight adhesion (S) can also be given.

Creep properties were determined at 120° C. by clamping film strips having a thickness from about 5 mils to about 15 mils in a temperature controlled oven and loading with weights to produce a stress of about 27 psi. After loading for 40 minutes, the film strips were removed and the dimensional changes in a pre-marked one inch gap were recorded.

The film is capable of being sealed using standard heat sealing techniques. An adequate heat seal is formed when a fluid container, such as the one shown in FIG. 3, is fabricated from the film by sealing peripheral edges to define a centrally disposed fluid chamber. The container is filled with water and subjected to a standard autoclave sterilization process. Adequate heat seals remain intact upon completion of the autoclave cycle.

The films of the present invention have a haze of less than about 25% and most preferably less than about 15% when measured in accordance with ASTM D1003. For the purposes of this invention, internal haze is defined as the haze value measured when both film surfaces have been wetted with isopropyl alcohol.

II. Polymer and Film Processing

To produce the film of the present invention, raw materials are fed into an extrusion hopper at the desired mix ratio employing weight feeders. The materials are extruded using an extrusion die to produce a mono-layer film. The film is irradiated with a suitable energy source and then sealed to form a fluid container. It is also contemplated exposing the blend to radiation before extrusion. The raw materials can also be pre-compounded before extrusion employing a single screw, twin screw or other compounding methods familiar to those skilled in the art.

The preferred method of irradiating the film is to expose it to an electron beam with beam energy from about 150 Kev–10 Mev, more preferably from 200–300 Kev and a dosage from about 20 kGys to about 200 kGys and more preferably from about 60–150 kGys. Alternatively, the film can be crosslinked using methods known to those skilled in the arts. Methods for crosslinking employed in the industry include exposure to ionizing radiation (gamma, beta, ultra-violet, etc.) and chemical (peroxides and condensing reactions).

To reduce or minimize the oxidative degradation of the film during and subsequent to electron beam exposure, it is desirable to reduce the partial pressure of oxygen in the area surrounding the film being exposed to the radiation. The oxygen partial pressure may be reduced by applying a vacuum or by applying another gas such as nitrogen under pressure or other known techniques for accomplishing this goal. In a preferred form of the invention the oxygen concentration during a nitrogen flush is less than about 100 ppm and more preferably less than about 40 ppm.

III. Multilayer Films

FIG. 2 shows an example of a multilayer film 20 including layer 12 of the mono-layer described above. In a preferred form of the invention the mono-layer shall be the seal layer. The multilayer film 20 can include any additional layer 14 or combination of additional layers selected from layers such as a skin layer, a radio frequency susceptible layer, a water vapor barrier layer, a gaseous barrier layer, a scrap layer, a seal layer and a core layer to name a few.

The skin layer can be added to increase the scuff resistance of the film. The skin layer can be an olefin material such as homopolymers and copolymers of propylene and ethylene. The skin layer may also be a polyester, copolyester, polyamide or copolyamide. The term "copolyester" and the like is applied to polyesters synthesized from more than one diol and a dibasic acid. Copolyesters as used herein may also be characterized as copolymers of polyether and polyethylene terephthalate. More preferably copolyesters as used herein may be characterized as polymeric materials derived from 1,4 cyclohexane dimethanol, 1,4 cyclohexane dicarboxylic acid, and polytetramethylene glycol ether, or equivalents of any of the above, as reactants.

Suitable water vapor barriers include but are not limited to HDPE, MDPE and polyester (PET, PBT, PEN, etc.)

Suitable gaseous barriers are those that inhibit the passage of oxygen, carbon dioxide or other gasses. Suitable gas barriers include but are not limited to polyesters and polyamides.

Scrap material generated prior to irradiation can be incorporated into one or more layers.

IV. Flowable Material Containers

FIG. 3 shows a flowable material container and particularly an I.V. container 30. FIG. 4 shows an I.V. administration set 40 and FIG. 5 shows a peritoneal dialysis set 50. The present invention further contemplates fabricating medical tubing from the blends of the present invention. It is contemplated that the radiation treatment of tubing will differ from films due to the increased thickness and round shape of tubing but tubing can be effectively treated within the radiation energy ranges set forth above for the film. What is meant by "flowable material" is a material that will flow by the force of gravity. Flowable materials therefore include both liquid items and powdered or granular items and the like. The container 30 has sidewalls 32 placed in registration and sealed along peripheral edges to define a chamber 34 for containing flowable materials such as fluids or granular material. For containers made through blow molding only or blow extrusion longitudinal edges would be sealed. A port tube 36 or multiple port tubes are provided to fill and empty the contents of the container 30. The sidewalls and port tube can be fabricated from one of the monolayer or multiple layered films set forth above. Surprisingly, the medical articles fabricated from the films and blends described above can be heat sealed even though the film has been irradiated with electron beam radiation.

Heat seals can be achieved using standard heat sealing techniques known to those skilled in the art.

V. Dual Chamber Peelable Seal Containers

Figure 6:
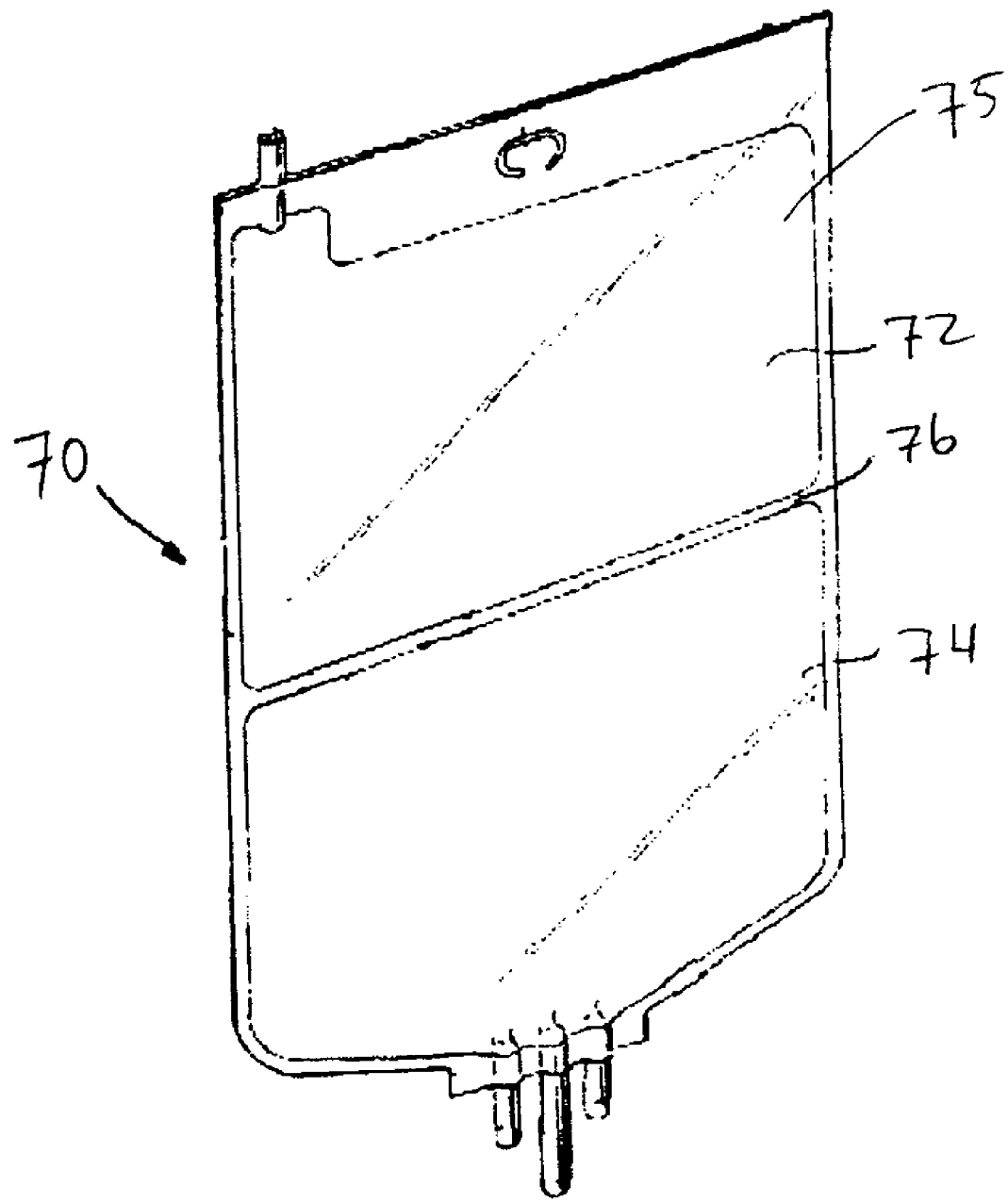
FIG. 6 is a dual chamber bag with a peelable seal separating the chambers.

FIG. 6 shows a dual chamber container 70 having a first chamber 72 and a second chamber 74 separated by a peelable seal 76. The container sidewalls 75 are fabricated from one of the polymer blends, monolayer films or multiple layered films set forth above. Dual chamber containers can be used for numerous applications such as separately housing two components for mixing later. The components can be liquid or powdered. The peelable seal can be created by modifying the sealing conditions such that the peelable seal 76 is capable of being ruptured by applying a force to a sidewall 75 of the container. Typically, one of the chambers will contain a liquid. By pressing on the container sidewall 75 over the liquid containing chamber the liquid contents will flow toward the peelable seal 76 and by applying sufficient pressure the seal 76 will rupture to allow mixing of the components stored in the separate chambers.

While FIG. 6 shows only one peelable seal 76, it is contemplated that numerous peelable seals could be provided to create numerous chambers. Further, FIG. 6 shows the peelable seal running between lateral edges. It is also contemplated that the peelable seals could extend between longitudinal edges or simply around an area not intersecting the permanent peripheral seam 79 to define a chamber.

The peelable seal 76 may be created simultaneously with sealing the peripheral sidewalls or before or after the creation of the permanent peripheral seals. The peelable seal 76 can be created by controlling sealing conditions. Peelable seals can be created with the application of lower temperature and pressure than employed to provide the permanent peripheral seal or by shortening the sealing times from that used to provide the permanent seal or the like. Further enhancement of the peel characteristics can be obtained with localized modification of the film surface characteristics (corona or other suitable treatment).

It is contemplated that the container can be sealed using ultrasonic welding techniques, conduction heat sealing techniques and other sealing techniques well known in the art.

VI. Examples

The blends identified in the table below were fabricated into a monolayer film using an extrusion process. The film was exposed to electron beam radiation having an acceleration voltage of from 200 Kev to 300 Kev for a dose set forth in the table that follows:

Dow Affinity PL 1880 is a ULDPE having a density of 0.902 g/cc.
DuPont Dow Engage 8003 is a ULDPE having a density of 0.885 g/cc.
Exxon PP305GE1 is a homopolymer of propylene (MFR 440).
Montell SA-861 is a propylene and ethylene copolymer (MFR 6.5).
Montell SA 982 is a propylene and ethylene copolymer (MFR 100).
"NA" means not available.

We claim:

1. A crosslinked non-diene containing polymer for fabricating monolayer films or a layer within a multilayer film, the polymer comprising:
   a blend composed solely of a first component and a second component, the first component selected from the group consisting of: (1) ethylene and α-olefin copolymers having a density of less than about 0.915 g/cc, and (2) ionomers, the first component being present in an amount from about 99% to about 55% by weight of the blend;
   the second component present in an amount by weight of the blend from about 45% to about 1% and selected from the group consisting of: (1) propylene containing polymers, (2) polybutene polymers, and (3) polymethylpentene polymers; and,

| FORMULA | 1 | 2 | 3 | 4 | 5 | 6 | 7 | 8 | 9 | 10 |
|---|---|---|---|---|---|---|---|---|---|---|
| DuPont/Dow Engage 8003 | 100 | 95 | 90 | 80 | | | | | | 70 |
| Dow Affinity PL-1880 | | | | | 100 | 95 | 90 | 80 | 70 | |
| Exxon PP3505GE1 | | 5 | 10 | 20 | | | | | | |
| Montell SA-861 | | | | | | 5 | 10 | 20 | 30 | 20 |
| Montell SG-982 | | | | | | | | | | 10 |
| Self adhesion rank — | | | | | | | | | | |
| 100 kGy | 1 | 2 | 3.7 | 4 | 1 | NA | 1 | 2 | 4 | NA |
| 150 kGy | 1 | 2 | 4.5 | 5 | 1 | NA | 1.3 | 2.3 | 3.3 | NA |
| 200 kGy | 1 | 3.3 | 4.7 | 5 | 1 | 1.7 | 2 | 2 | 4 | NA |
| Tack to over pouch — | | | | | | | | | | |
| 100 kGy | Y | S | N | N | Y | NA | Y | S | N | NA |
| 150 kGy | Y | S | N | N | Y | NA | Y | N | N | NA |
| 200 kGy | Y | S | N | N | Y | NA | Y | N | N | NA |
| 120° C. Creep (%) | | | | | | | | | | |
| 0 kGy | NA | NA | NA | NA | NA | NA | Melts | NA | 550 | NA |
| 100 kGy | 200 | 138 | 88 | 41 | 263 | NA | 216 | 98 | 28 | NA |
| 150 kGy | 63 | 38 | 31 | 18 | 43 | NA | 31 | 25 | 13 | NA |
| 200 kGy | 25 | 13 | 16 | 16 | 21 | 22 | 16 | 9 | 22 | NA |
| Autoclavability | | | | | | | | | | |
| 100 kGy | NA | NA | Y | Y | NA | NA | NA | Y | Y | Y |
| 150 kGy | NA | NA | Y | Y | NA | NA | NA | Y | Y | Y |
| Internal Haze (ASTM D1003) | 1 | 1.2 | 1.6 | 2.8 | 2.7 | 2.7 | 3.5 | 4.3 | 4.8 | 2.2 |
| Tensile modulus (psi) (ASTM D882) | 2860 | 3800 | 6650 | 16260 | 6110 | NA | 12830 | 19810 | 28820 | 21060 |

Dow Affinity PL 1880 is a ULDPE having a density of 0.902 g/cc.
DuPont Dow Engage 8003 is a ULDPE having a density of 0.885 g/cc.
Exxon PP305GE1 is a homopolymer of propylene (MFR 440).
Montell SA-861 is a propylene and ethylene copolymer (MFR 6.5).
Montell SA 982 is a propylene and ethylene copolymer (MFR 100).
"NA" means not available.

the blend when fabricated into a film having a modulus of elasticity when measured in accordance with ASTM D882 of less than about 60,000 psi, an internal haze when measured in accordance with ASTM D1003 of less than about 25%, an internal adhesion ranking of greater than about 2, a sample creep at 120° C. under 27 psi loading of less than or equal to 150% for a film having a thickness of from about 5 mils to about 15 mils, and the film being capable of being heat sealed into a container having seals wherein the seals remain intact when the container is autoclaved at 121° C. for one hour.

2. The blend of claim 1 wherein the propylene containing polymer is selected from the group consisting of homopolymers of polypropylene, and random and block copolymers and random and block terpolymers of propylene with one or more comonomers selected from α-olefin having from about 2 to about 17 carbons.

3. The blend of claim 2 wherein the second component is a propylene and ethylene copolymer having an ethylene content of from 1–6% by weight of the copolymer.

4. The blend of claim 2 wherein the second component is a blend of a first propylene containing polymer and a second propylene containing polymer.

5. The blend of claim 4 wherein the first propylene containing polymer has a first melt flow rate and the second propylene containing polymer has a second melt flow rate wherein the first melt flow rate is about 3 times greater than the second melt flow rate.

6. The blend of claim 4 wherein the first propylene containing polymer has a first melt flow rate and the second propylene containing polymer has a second melt flow rate wherein the first melt flow rate is about 5 times greater than the second melt flow rate.

7. The blend of claim 4 wherein the first propylene containing polymer has a first melting point temperature and the second propylene containing polymer has a second melting point temperature wherein the first melting point temperature is higher than the second melting point temperature by at least about 5° C.

8. The blend of claim 4 wherein the first propylene containing polymer has a first melting point temperature and the second propylene containing polymer has a second melting point temperature wherein the first melting point temperature is higher than the second melting point temperature by at least about 10° C.

9. The blend of claim 1 wherein the α-olefin has from 3 to 17 carbons.

10. The blend of claim 1 wherein the α-olefin has from 4 to 8 carbons.

11. The blend of claim 10 wherein the ethylene and α-olefin copolymer is obtained using a single site catalyst.

12. The blend of claim 1 wherein the blend is subjected to electron beam radiation in a dosage amount from about 20 kGy to about 200 kGy.

13. The blend of claim 1 wherein the internal haze when measured in accordance with ASTM D1003 is less than 15%.

14. A crosslinked non-diene containing polymer for fabricating monolayer films or a layer within a multilayer film comprising:
a blend composed solely of a first component and a second component, the first component selected from the group consisting of: (1) ethylene and α-olefin copolymers having a density of less than about 0.915 g/cc, and (2) ionomers, the first component being present in an amount from about 99% to about 55% by weight of the blend;
the second component present in an amount by weight of the blend from about 45% to about 1% and selected from the group consisting of: (1) propylene containing polymers, (2) polybutene polymers, and (3) polymethylpentene polymers; and,
wherein the blend is subjected to electron beam radiation in a dosage amount from about 20 kGy to about 200 kGy.

15. The blend of claim 14 wherein the blend when fabricated into a film having a modulus of elasticity when measured in accordance with ASTM D882 of less than about 60,000 psi, an internal haze when measured in accordance with ASTM D1003 of less than about 25%, an internal adhesion ranking of greater than about 2, a sample creep at 120° C. under 27 psi loading of less than or equal to 150% for a film having a thickness of from about 5 mils to about 15 mils, and the film being capable of being heat sealed into a container having seals wherein the seals remain intact when the container is autoclaved at 121° C. for one hour.

16. The blend of claim 14 wherein the blend is exposed to an oxygen partial pressure less than ambient conditions when exposed to the electron beam radiation.

17. The blend of claim 14 wherein the propylene containing polymer is selected from the group consisting of homopolymers of polypropylene, and random and block copolymers and random and block terpolymers of propylene with one or more comonomers selected from α-olefins having from about 2 to about 17 carbons.

18. The blend of claim 14 wherein the second component is a propylene and ethylene copolymer having an ethylene content of from 1–6% by weight of the copolymer.

19. The blend of claim 14 wherein the second component is a blend of a first propylene containing polymer and a second propylene containing polymer.

20. The blend of claim 19 wherein the first propylene containing polymer has a first melt flow rate and the second propylene containing polymer has a second melt flow rate wherein the first melt flow rate is about 3 times greater than the second melt flow rate.

21. The blend of claim 19 wherein the first propylene containing polymer has a first melt flow rate and the second propylene containing polymer has a second melt flow rate wherein the first melt flow rate is about 5 times greater than the second melt flow rate.

22. The blend of claim 19 wherein the first propylene containing polymer has a first melting point temperature and the second propylene containing polymer has a second melting point temperature wherein the first melting point temperature is higher than the second melting point temperature by at least about 5° C.

23. The blend of claim 19 wherein the first propylene containing polymer has a first melting point temperature and the second propylene containing polymer has a second melting point temperature wherein the first melting point temperature is higher than the second melting point temperature by at least about 10° C.

24. The blend of claim 14 wherein the α-olefin has from 3 to 17 carbons.

25. The blend of claim 14 wherein the α-olefin has from 4 to 8 carbons.

26. The blend of claim 24 wherein the ethylene and α-olefin copolymer is obtained using a single site catalyst.

27. A crosslinked non-diene containing monolayer film comprising:
a blend composed solely of a first component and a second component, the first component selected from the group consisting of: (1) ethylene and α-olefin copolymers having a density of less than about 0.915 g/cc, and (2) ionomers, the first component being present in an amount from about 99% to about 55% by weight of the blend;
the second component present in an amount by weight of the blend from about 45% to about 1% and selected from the group consisting of: (1) propylene containing polymers, (2) polybutene polymers, and (3) polymethylpentene polymers; and,
the film has a modulus of elasticity when measured in accordance with ASTM D882 of less than about 60,000 psi, an internal haze when measured in accordance with ASTM D1003 of less than about 25%, an internal adhesion ranking of greater than about 2, a sample creep at 120° C. under 27 psi loading of less than or equal to 150% for a film having a thickness of from about 5 mils to about 15 mils, and the film being capable of being heat sealed into a container having seals wherein the seals remain intact when the container is autoclaved at 121° C. for one hour.

28. The film of claim 27 wherein the propylene containing polymer is selected from the group consisting of homopolymers of polypropylene, and random and block copolymers and random and block terpolymers of propylene with one or more comonomers selected from α-olefins having from about 2 to about 17 carbons.

29. The film of claim 28 wherein the second component is a propylene and ethylene copolymer having an ethylene content of from 1–6% by weight of the copolymer.

30. The film of claim 28 wherein the second component is a blend of a first propylene containing polymer and a second propylene containing polymer.

31. The film of claim 30 wherein the first propylene containing polymer has a first melt flow rate and the second propylene containing polymer has a second melt flow rate wherein the first melt flow rate is about 3 times greater than the second melt flow rate.

32. The film of claim 30 wherein the first propylene containing polymer has a first melt flow rate and the second propylene containing polymer has a second melt flow rate wherein the first melt flow rate is about 5 times greater than the second melt flow rate.

33. The film of claim 30 wherein the first propylene containing polymer has a first melting point temperature and the second propylene containing polymer has a second melting point temperature wherein the first melting point temperature is higher than the second melting point temperature by at least about 5° C.

34. The film of claim 30 wherein the first propylene containing polymer has a first melting point temperature and the second propylene containing polymer has a second melting point temperature wherein the first melting point temperature is higher than the second melting point temperature by at least about 10° C.

35. The film of claim 27 wherein the α-olefin has from 3 to 17 carbons.

36. The film of claim 27 wherein the α-olefin has from 4 to 8 carbons.

37. The film of claim 36 wherein the ethylene and α-olefin copolymer is obtained using a single site catalyst.

38. The film of claim 27 wherein the blend is subjected to electron beam radiation in a dosage amount from about 20 kGy to about 200 kGy.

39. The film of claim 27 wherein the internal haze when measured in accordance with ASTM D 1003 is less than 15%.

40. A crosslinked non-diene containing monolayer film comprising:
- a blend composed solely of a first component and a second component, the first component selected from the group consisting of: (1) ethylene and α-olefin copolymers having a density of less than about 0.915 g/cc, and (2) ionomers, the first component being present in an amount from about 99% to about 55% by weight of the film;
- the second component present in an amount by weight of the film from about 45% to about 1% and selected from the group consisting of: (1) propylene containing polymers, (2) polybutene polymers, and (3) polymethylpentene polymers; and,
- wherein the film is subjected to electron beam radiation in a dosage amount from about 20 kGy to about 200 kGy, and is capable of being heat sealed into a container having seals wherein the seals remain intact when the container is autoclaved at 121° C. for one hour.

41. The film of claim 40 has a modulus of elasticity when measured in accordance with ASTM D882 of less than about 60,000 psi, an internal haze when measured in accordance with ASTM D1003 of less than about 25%, an internal adhesion ranking of greater than about 2, a sample creep at 120° C. under 27 psi loading of less than or equal to 150% for a film having a thickness of from about 5 mils to about 15 mils, and the film being capable of being heat sealed into a container having seals wherein the seals remain intact when the container is autoclaved at 121° C. for one hour.

42. The film of claim, 40 wherein the film is exposed to a oxygen partial pressure less than ambient conditions when exposed to the electron beam radiation.

43. The film of claim 40 wherein the propylene containing polymer is selected from the group consisting of homopolymers of polypropylene, and random and block copolymers and random and block terpolymers of propylene with one or more comonomers selected from α-olefins having from about 2 to about 17 carbons.

44. The film of claim 40 wherein the second component is a propylene and ethylene copolymer having an ethylene content of from 1–6% by weight of the copolymer.

45. The film of claim 40 wherein the second component is a blend of a first propylene containing polymer and a second propylene containing polymer.

46. The film of claim 45 wherein the first propylene containing polymer has a first melt flow rate and the second propylene containing polymer has a second melt flow rate wherein the first melt flow rate is about 3 times greater than the second melt flow rate.

47. The film of claim 45 wherein the first propylene containing polymer has a first melt flow rate and the second propylene containing polymer has a second melt flow rate wherein the first melt flow rate is about 5 times greater than the second melt flow rate.

48. The film of claim 45 wherein the first propylene containing polymer has a first melting point temperature and the second propylene containing polymer has a second melting point temperature wherein the first melting point temperature is higher than the second melting point temperature by at least about 5° C.

49. The film of claim 45 wherein the first propylene containing polymer has a first melting point temperature and the second propylene containing polymer has a second melting point temperature wherein the first melting point temperature is higher than the second melting point temperature by at least about 10° C.

50. The film of claim 40 wherein α-olefin has from 3 to 17 carbons.

51. The film of claim 40 wherein the α-olefin has from 4 to 8 carbons.

52. The film of claim 50 wherein the ethylene and α-olefin copolymer is obtained using a single site catalyst.

53. A method for preparing a non-oriented, non-diene and non-PVC containing film comprising the steps of:
- providing a first component selected from the group consisting of: (1) ethylene and α-olefin copolymers having a density of less than about 0.915 g/cc, and (2) ionomers, the first component being present in an amount from about 99% to about 55% by weight of the blend;
- providing a second component in an amount by weight of the blend from about 45% to about 1% and is selected from the group consisting of: (1) propylene containing polymers, (2) polybutene polymers, and (3) polymethylpentene polymers;
- mixing the first component and the second component to define a blend;
- crosslinking a portion of the blend; and
- processing the blend into a monolayer film having a modulus of elasticity when measured in accordance with ASTM D882 of less than about 60,000 psi, an internal haze when measured in accordance with ASTM D 1003 of less than about 25%, an internal adhesion ranking of greater than about 2, a sample creep at 120° C. under 27 psi loading of less than or equal to 150% for a film having a thickness of from about 5 mils to about 15 mils, and the film being capable of being heat sealed into a container having seals wherein the seals remain intact when the container is autoclaved at 121° C. for one hour.

54. The method of claim 53 wherein the propylene containing polymer is selected from the group consisting of homopolymers of polypropylene, and random and block copolymers and random and block terpolymers of propylene with one or more comonomers selected from α-olefins having from about 2 to about 17 carbons.

55. The blend of claim 53 wherein the second component is a propylene and ethylene copolymer having an ethylene content of from 1–6% by weight of the copolymer.

56. The method of claim 53 wherein the second component is a blend of a first propylene containing polymer and a second propylene containing polymer.

57. The method of claim 53 wherein the first propylene containing polymer has a first melt flow rate and the second propylene containing polymer has a second melt flow rate wherein the first melt flow rate is about 3 times greater than the second melt flow rate.

58. The method of claim 56 wherein the first propylene containing polymer has a first melt flow rate and the second propylene containing polymer has a second melt flow rate wherein the first melt flow rate is about 5 times greater than the second melt flow rate.

59. The method of claim 56 wherein the first propylene containing polymer has a first melting point temperature and the second propylene containing polymer has a second melting point temperature wherein the first melting point temperature is higher than the second melting point temperature by at least about 5° C.

60. The method of claim 56 wherein the first propylene containing polymer has a first melting point temperature and the second propylene containing polymer has a second melting point temperature wherein the first melting point temperature is higher than the second melting point temperature by at least about 10° C.

61. The method of claim 53 wherein the α-olefin has from 3 to 17 carbons.

62. The method of claim 53 wherein the α-olefin has from 4 to 8 carbons.

63. The method of claim 62 wherein the ethylene and α-olefin copolymer is obtained using a single site catalyst.

64. The method of claim 53 wherein the crosslinking further comprises exposing the blend to electron beam radiation in a dosage amount from about 20 KGy to about 200 kGy.

65. The method of claim 53 wherein the step of processing the blend into a monolayer film comprises the step of extruding the blend.

66. A method for fabricating a non-diene monolayer film or a layer within a multilayer film comprising:
providing a first component selected from the group consisting of: (1) ethylene and α-olefin copolymers having a density of less than about 0.915 g/cc, and (2) ionomers, the first component being present in an amount from about 99% to about 55% by weight of the blend;
providing a second component in an amount by weight of the blend from about 45% to about 1% and is selected from the group consisting of: (1) propylene containing polymers, (2) polybutene polymers, and (3) polymethylpentene polymers;
mixing the first component with the second component to define a blend;
processing the blend into a monolayer film or a layer within a multiple layered film to define a structure; and,
crosslinking the structure with electron beam radiation in a dosage amount from about 20 kGy to about 200 kGy.

67. The method of claim 66 wherein the film has a modulus of elasticity when measured in accordance with ASTM D882 of less than about 60,000 psi, an internal haze when measured in accordance with ASTM D1003 of less than about 25%, an internal adhesion ranking of greater than about 2, a sample creep at 120° C. under 27 psi loading of less than or equal to 150% for a film having a thickness of from about 5 mils to about 15 mils, and the film being capable of being heat sealed into a container having seals wherein the seals remain intact when the container is autoclaved at 121° C. for one hour.

68. The method of claim 66 wherein the crosslinking includes the step of reducing an oxygen partial pressure to less than ambient conditions.

69. The method of claim 66 wherein the propylene containing polymer is selected from the group consisting of homopolymers of polypropylene, and random and block copolymers and random and block terpolymers of propylene with one or more comonomers selected from α-olefins having from about 2 to about 17 carbons.

70. The method of claim 66 wherein the second component is a propylene and ethylene copolymer having an ethylene content of from 1–6% by weight of the copolymer.

71. The method of claim 66 wherein the second component is a blend of a first propylene containing polymer and a second propylene containing polymer.

72. The method of claim 71 wherein the first propylene containing polymer has a first melt flow rate and the second propylene containing polymer has a second melt flow rate wherein the first melt flow rate is about 3 times greater than the second melt flow rate.

73. The method of claim 71 wherein the first propylene containing polymer has a first melt flow rate and the second propylene containing polymer has a second melt flow rate wherein the first melt flow rate is about 5 times greater than the second melt flow rate.

74. The method of claim 71 wherein the first propylene containing polymer has a first melting point temperature and the second propylene containing polymer has a second melting point temperature wherein the first melting point temperature is higher than the second melting point temperature by at least about 5° C.

75. The method of claim 71 wherein the first propylene containing polymer has a first melting point temperature and the second propylene containing polymer has a second melting point temperature wherein the first melting point temperature is higher than the second melting point temperature by at least about 10° C.

76. The method of claim 66 wherein the α-olefin has from 3 to 17 carbons.

77. The method of claim 66 wherein the α-olefin has from 4 to 8 carbons.

78. The method of claim 77 wherein the ethylene and α-olefin copolymer is obtained using a single site catalyst.

79. The method of claim 66 wherein the step of processing the blend includes the step of extruding the blend into a film or a layer within a multiple layered film.

* * * * *